US011504462B2

(12) United States Patent
Hyde et al.

(10) Patent No.: US 11,504,462 B2
(45) Date of Patent: Nov. 22, 2022

(54) MEDICAL DEVICE

(71) Applicant: Maquet Cardiopulmonary GmbH, Rastatt (DE)

(72) Inventors: Aidan Hyde, Collingswood, NJ (US); Robert Hoff, Boonton, NJ (US); Daniel Medart, Stahnsdorf (DE); Daniel A. Walters, Rockaway Township, NJ (US)

(73) Assignee: Maquet Cardiopulmonary GmbH, Rastatt (DE)

( * ) Notice: Subject to any disclaimer, the term of this patent is extended or adjusted under 35 U.S.C. 154(b) by 1200 days.

(21) Appl. No.: 15/766,761

(22) PCT Filed: Oct. 7, 2016

(86) PCT No.: PCT/US2016/056195
§ 371 (c)(1),
(2) Date: Apr. 6, 2018

(87) PCT Pub. No.: WO2017/062921
PCT Pub. Date: Apr. 13, 2017

(65) Prior Publication Data
US 2018/0289886 A1 Oct. 11, 2018

Related U.S. Application Data

(60) Provisional application No. 62/336,571, filed on May 13, 2016, provisional application No. 62/238,358, filed on Oct. 7, 2015.

(51) Int. Cl.
*A61M 1/36* (2006.01)
*A61M 1/16* (2006.01)
*A61M 60/00* (2021.01)

(52) U.S. Cl.
CPC ........ *A61M 1/3666* (2013.01); *A61M 1/1698* (2013.01); *A61M 60/00* (2021.01);
(Continued)

(58) Field of Classification Search
CPC .............. A61M 1/3666; A61M 1/3667; A61M 1/1698; A61M 60/00; A61M 2209/08; A61M 2209/082; A61M 2209/084
See application file for complete search history.

(56) References Cited

U.S. PATENT DOCUMENTS 5,216,579 A 6/1993 Basara et al.
6,037,538 A * 3/2000 Brooks .................. H02G 3/288
174/498
(Continued)

FOREIGN PATENT DOCUMENTS

EP 0477551 A1 4/1992
EP 1396235 A1 3/2004
(Continued)

OTHER PUBLICATIONS

Translation of JP 2014046026; retrieved from JPO website on Jul. 17, 2021 (Year: 2014).*
(Continued)

*Primary Examiner* — Philip R Wiest

(57) ABSTRACT

A cardiopulmonary bypass system is described that includes a cardiopulmonary bypass machine having a console, the console has a base and a frame connected to the base. The system further comprises a plurality of peripheral modules operatively connectable to the cardiopulmonary bypass machine via one or more cables. The system further comprises a cable chase having a first end and a second end, and a housing that extends at least partially between the first end and second end to at least partially enclose a channel for receiving one or more cables or conduits connected to one or more of the peripheral modules.

31 Claims, 16 Drawing Sheets

(52) U.S. Cl.
    CPC ... *A61M 2209/08* (2013.01); *A61M 2209/082* (2013.01); *A61M 2209/084* (2013.01)

(56) References Cited

U.S. PATENT DOCUMENTS

| | | | |
|---|---|---|---|
| 6,071,258 A * | 6/2000 | Dalke | A61M 1/3621 422/44 |
| 6,197,197 B1 | 3/2001 | Peterson et al. | |
| 8,138,419 B2 | 3/2012 | Garza et al. | |
| 2006/0122551 A1 | 6/2006 | Brieske | |

FOREIGN PATENT DOCUMENTS

| | | | |
|---|---|---|---|
| ES | 2332964 A1 | 2/2010 | |
| JP | 2004514478 A | 5/2004 | |
| JP | 2014/046026 * | 3/2014 | A61M 1/00 |
| JP | 2014-046026 A | 3/2014 | |

OTHER PUBLICATIONS

International Search Report dated Dec. 30, 2016 for corresponding PCT application No. PCT/US2016/056195 filed Oct. 7, 2016, 3 pages.
Maquet Getinge Group, Informational Brochure, "Sprinter Cart XL: Ready to Move When You Are", 2 pages (Mar. 2013).
Extended European Search Report dated Mar. 28, 2019 for corresponding EP application No. 16854523.4, 8 pages.
Maquet Getinge Group, Informational Brochure, "Cardiohelp System Extracorporeal Support Solution", 10 pages, (Mar. 2013).
Office Action issued in Japanese Application No. 2018-517843 dated Oct. 1, 2020, 9 pages.
Office Action issued in Chinese Application No. 201680058385.4 dated Dec. 11, 2020, 20 pages.
Office Action and Search Report issued in counterpart Chinese Application No. 2016800583854 dated Apr. 17, 2020, 19 pages (Only Translation of Office Action included).

* cited by examiner

MEDICAL DEVICE

This application is a national stage application of International Application No. PCT/US2016/056195, filed Oct. 7, 2016, and claims the benefit of priority to U.S. Provisional Patent Application No. 62/238,358, filed Oct. 7, 2015, and U.S. Provisional Patent Application No. 62/336,571, filed May 13, 2016. The disclosures of International Application No. PCT/US2016/056195, U.S. Provisional Patent Application No. 62/238,358, and U.S. Provisional Patent Application No. 62/336,571 are herein incorporated by reference in their entireties.

FIELD OF THE DISCLOSURE

The present disclosure pertains to the field of medical devices involving peripheral modules, including systems, equipment, related accessories, and components that generally involve the conveyance of data, fluid and energy through a variety of cables, cords, wires, and/or conduits.

More specifically, the present disclosure may pertain to extracorporeal fluid support and transport systems, such as perfusion systems, also known as "heart-lung" machines and cardiopulmonary bypass machines.

BACKGROUND OF THE DISCLOSURE

There is an ever evolving need for new and improved solutions to medical apparatuses that utilize a number of various electronic and/or motorized modules, especially those that are required to be rearranged, replaced, added to, or removed from a main console machine during use in the surgical setting, whether by plan or in an unplanned manner. Some of the modules may have a direct physical and electrical connection to a main console, while others may be indirectly attached and powered or controlled remotely by wires and cables. Within the field of cardiopulmonary perfusion, the rearrangement of the modules to a primary chassis and frame of a heart-lung machine may need to occur prior to and during use of such machines. If a need arises during use requiring a change to the arrangement of components or use of certain components during a surgical procedure, such an interruption may be inconvenient, add extra time and cost to the overall surgery, and may complicate the delivery of care to the patient. With highly specialized procedures such an on-pump CAGB surgical procedure, such interruptions are especially undesirable to the surgical team involved with the CABG procedure.

Perfusion systems involve a wide variety of components and accessories that are dependent on the patient's needs, the operator's preferences for operational setup, availability of modular hardware (e.g., console pumps, mast-mounted pumps, pump displays and controllers, etc.), and the use of various sensors and diagnostic equipment. Prior to carrying out a cardiac surgery, perfusionists may arrange their equipment into one of an extensive number of permutations that are meant to address the needs for the patient that will undergo surgery. Due to the extensive use of cables, blood conduits, pumps, pump displays, and other related devices that commonly are involved with such procedures, the cables and cords may become heavily intertwined and difficult to manage. This may lead to specific issues of operational inconvenience and time inefficiency for the perfusionist.

As heart-lung machines often involve the usage of a wide variety of peripheral modules that need to be controlled through the user interface of the heart-lung machine, and given that any one of the peripherals may need to be switched out and replaced for various reasons, including but not limited a change in the delivery of therapy, or unexpected failure of the unit (whether electrical or mechanical), there is a need to be able to quickly replace the peripheral so that the perfusionist can attend to the delivery of cardiac support to the patient and minimize any downtime associated with the failure. When the peripheral is unable to be quickly switched out due to the routing of cables and wires, additional complications may occur.

Therefore, there is a need for medical equipment such as heart-lung machines to have improved features that permit the user to simplify the reconfiguring, set up and management of their systems.

SUMMARY OF THE DISCLOSURE

This disclosure is directed to describing embodiments, apparatuses and methods that overcome certain deficiencies of conventional heart-lung machines and their operational setups.

In accordance with a first non-limiting embodiment of this disclosure, a cardiopulmonary bypass system includes (a) a cardiopulmonary bypass machine having a console, the console having a base and a frame connected to the base, (b) a plurality of peripheral modules operatively connectable to the cardiopulmonary bypass machine; and (c) a cable chase comprising a first end and a second end, and housing that extends at least partially between the first end and second end at least partially encloses a channel for receiving one or more cables or conduits connected to at least one of the peripheral modules.

According to an example embodiment, the peripheral modules are selected from one or more of the following: (a) console pumps, (b) mast mounted pumps, (c) occlusion clamps, (d) display monitors, and (e) pump control monitors.

According to an example embodiment, the one or more of the console and mast mounted pumps may be either roller pumps or centrifugal pumps, or combinations thereof.

According to an example embodiment, the frame has one or more masts connected to and extending vertically with respect to the base.

According to an example embodiment disclosed herein, the cable chase housing may have two or more apertures spaced apart from each other for cables to enter and exit the channel at different locations along a length of the cable chase housing.

According to an example embodiment, the distance between a first of the two or more apertures and a second of the two or more apertures is greater than 4 inches, more preferably greater than 10 inches, or alternatively greater than 15 inches.

According to an example embodiment disclosed herein, the housing may have a length that is greater than 5.0 inches, more preferably greater than 10 inches, even more preferably greater than 20 inches, more preferably greater than 25 inches, and even more preferably greater than 30 inches, and alternatively greater than 40 inches.

According to an example embodiment disclosed, the cable chase may further comprising a cover, wherein the cover may be configured to at least partially and reversibly enclose a lengthwise portion of the channel. Additionally, the cover may be elongate and extend from the first end towards the second end of the cable chase. Further, the cover may extend the entire length of the cable chase.

According to an example embodiment disclosed, the cover may removably be attached to the housing.

According to an example embodiment disclosed, the cover may be attached to the housing and opens and close with respect to the channel of the housing, thereby selectively enabling and restricting access to the channel.

According to an example embodiment disclosed, the cover may have a hook for reversibly attaching to an elongate rail of the cardiopulmonary bypass machine when the cable channel is affixed to the elongate rail.

According to an example embodiment, the base has a console pump support surface for supporting a plurality of console pumps, and wherein the frame comprises a shelf that is elevated with respect to the console pump support surface. Additionally, the cable channel may be configured to attach to one or both of the base and the frame.

According to an example embodiment disclosed, the base may comprise a console pump support surface for supporting a plurality of console pumps, and wherein the frame comprises a shelf that is elevated with respect to the console pump support surface. One or both of the base and the frame may be configured to attachably receive the cable chase.

According to an example embodiment disclosed, the cable chase may be mounted to the cardiopulmonary bypass machine such that the channel extends vertically between a first elevation and a second elevation higher than the first elevation. Further, when mounted to the cardiopulmonary bypass machine, the channel of the cable chase may extend vertically (e.g., lengthwise in the vertical direction).

According to an example embodiment disclosed, the cable chase is configured to be attached to the cardiopulmonary bypass machine at a plurality of locations that are horizontally disposed from each other. Optionally, the console may comprise one or more horizontally mounted elongate structures, and the cable chase may be configured to mount to at least one of the one or more horizontally mounted elongate structures.

According to an example embodiment disclosed, the cable chase is configured to simultaneously mount to at least two horizontally mounted elongate structures that are parallel yet spaced apart from each other. The elongate structures may be rails, and may have a cross-sectional profile such as a rectangular, circular, oval, elliptical, square, etc.

According to an example embodiment, the cable chase may be configured to mount to two horizontally mounted elongate structures simultaneously.

According to an example embodiment disclosed, at least one of the one or more horizontally mounted elongate structures may be a rail.

According to an example embodiment disclosed, two or more horizontally mounted elongate structures are provided, and wherein the cable chase is configured to simultaneously mount to both of the horizontally mounted elongate structures.

According to an example embodiment disclosed, the cable chase has a first connector, and the first connector is configured to permit the cable chase to be reversibly attached to the cardiopulmonary bypass machine.

According to an example embodiment, a second connector may be configured to permit the cable chase to be reversibly attached to the cardiopulmonary bypass machine at a location different than the first connector.

According to an example embodiment disclosed, one or both of the first and second connectors may be clamps.

According to an example embodiment disclosed, the second elongate structure is a rail, and the first elongate structure and the second elongate structure have consistent cross-sectional profile along more than half of their lengths, preferably their entire lengths.

According to an example embodiment disclosed, the system includes a first connector, wherein the first connector is configured to reversibly connect one of the cardiopulmonary bypass machine and the cable chase to the other of the cardiopulmonary bypass machine and the cable chase.

According to an example embodiment disclosed, a slot is located in at least one of the cover and the housing, and a protrusion on the other of the cover and the housing is arranged for aligning and mating with the slot when the cover and housing are arranged or otherwise brought together with respect to each other for the cover to at least partially enclose the channel of the housing. The slot may be open at one end and angled downwards towards a closed end of the slot such that the slot receives and retains the protrusion. The protrusion may be a pin, and may be mounted on either of an inner or outer surface of the sidewalls of the housing and/or cover.

According to an example embodiment, at least one of the housing and the cover of the cable chase may have a hook, and the other of the housing of the cover may have an aperture for receiving the hook when the cover is attached or otherwise brought into opposition to the housing of the cable chase.

According to an example embodiment disclosed, a cable holder is suspended from an underside of the shelf and may have a plurality of fingers extending upwards from a channel body to provide for one or more passages for cables or conduits to be secured underneath the shelf.

The features, objects, benefits and advantages of the present disclosure will become more apparent upon reading the following detailed description that follows pertaining to the exemplary embodiments. In the description, reference is made to the accompanying drawings, which form a part hereof and in which there is shown by way of illustration, not limitation, embodiments of the disclosure.

BRIEF DESCRIPTION OF THE DRAWING

FIG. 9B is a cross-sectional view taken along sectional lines 9B-9B of FIG. 8.

DETAILED DESCRIPTION OF THE DISCLOSED EMBODIMENT(S)

Figure 1A:
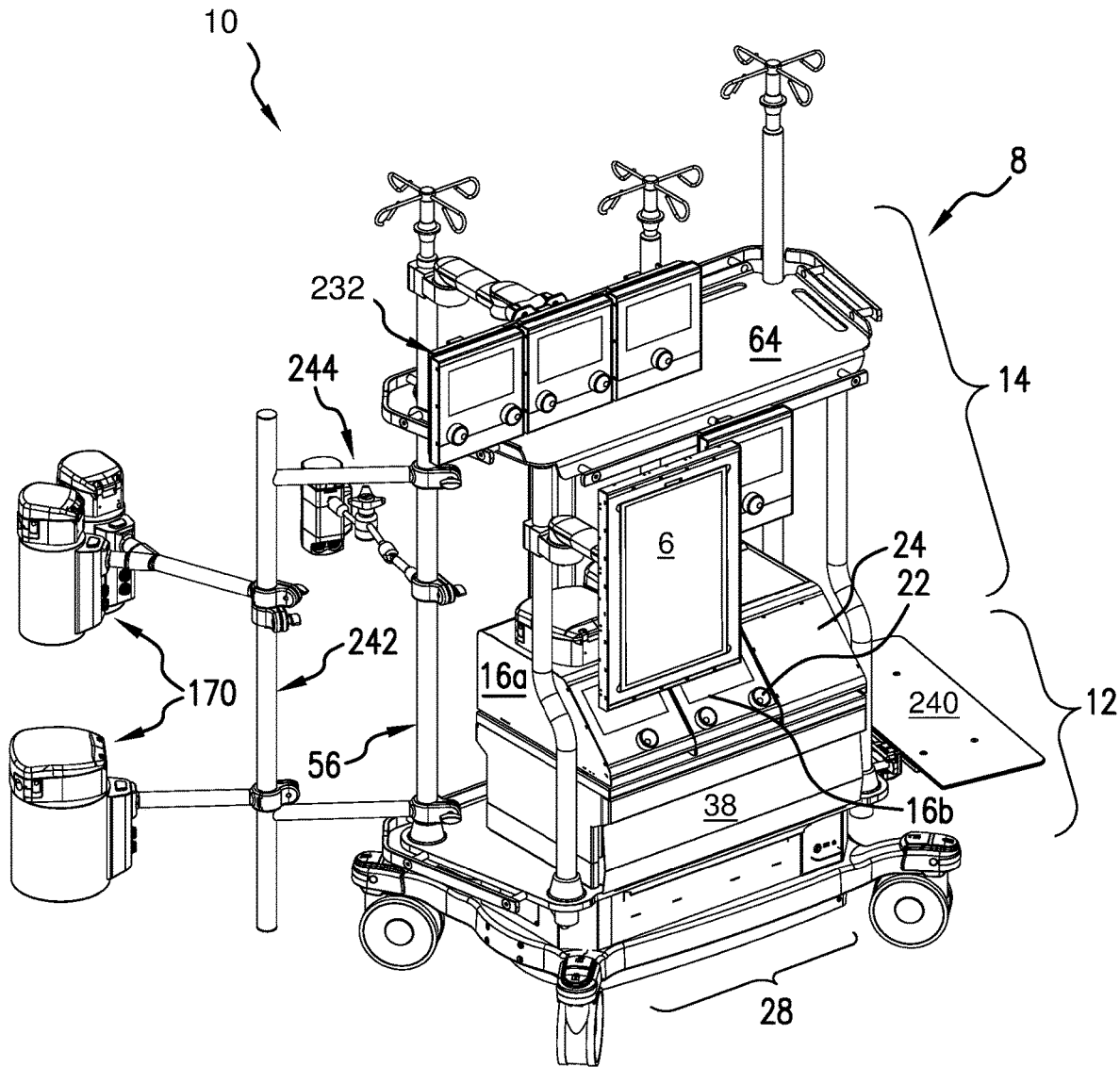
FIG. 1A is a perspective view of a medical apparatus in the form of a heart-lung machine, including various peripheral devices attached thereto, illustrating the "operator side" (i.e., or "perfusionist side") thereof, in accordance with an embodiment of the present disclosure.

Various embodiments in accordance with this disclosure are described with reference to the figures, in which like parts are designated by like reference numbers. The drawings described herein constitute non-limiting illustrations. For purposes of the description hereinafter, the words "upper," "lower," "right," "left," "vertical," "horizontal," "top," "bottom," "lateral," "longitudinal," "axial," and like terms, if used, shall relate to the invention, as it is oriented in the drawing figures. When appropriate, the term "patient side" shall refer to the side of an apparatus that typically is facing (or otherwise closest or most proximal to) a patient, such as a patient undergoing a cardiac surgical procedure in a surgical arena. The term "operator side" or "perfusionist side" shall refer to the side of an apparatus that typically is facing the operator of the apparatus, as would be the case for a perfusionist that is managing the operation of a heart-lung machine within a surgical arena, and generally opposite to the "patient side." It is to be understood that the invention may assume many alternative variations and embodiments except where expressly specified to the contrary. It is also to be understood that the specific devices and embodiments illustrated in the accompanying drawings and described herein are simply example embodiments of the disclosure.

FIGS. 1A through 5 illustrate a console 8 of a medical apparatus system 10, and more specifically illustrate by example an apparatus system 10 configured as a medical bypass machine such as a heart-lung machine (i.e., a cardiopulmonary bypass machine). The medical apparatus system however can additionally or alternatively be configured as a machine useful for extracorporeal fluid transport and therapy, such as any of a cardiac support, cardiac bypass, extra-corporeal membrane oxygenation (ECMO), apheresis, or a dialysis-type machine.

The medical apparatus system 10 comprises a console 8 is which is illustrated in FIG. 1A as having a base 12 (or base portion/chassis) and a frame 14 (or frame portion) that is connected to the base 12 and generally is mounted to be on top of the base 12. The base 12 may further house or support electrical components, cable connection ports, processors, batteries, power converters, and controllers useful for controlling, capturing data from, and managing power, machine instructions, and energy delivery to one or more modules. Examples of such modules include one or more console pumps 16, which are illustrated in FIG. 1A as either an individual pump module 16a or as a twin-pump console module 16b, and are shown resting on a console pump module support surface 96. Each of the two types of pump modules 16 have one or more roller pump heads 18 that comprise a raceway for receiving the tubing of one or more cardiopulmonary circuits. The console pump modules 16 further comprise an integral display 20 and one or more controls 22 for controlling their respective pump speeds and resulting flow rates of fluid conveyed through the tubing connected to the pumps. As shown in FIG. 1A, the pump modules 16 are arranged in a "piano-style" configuration, wherein adjacent pump modules are arranged in a generally parallel orientation with respect to adjacent console pump modules. This pattern may utilize two or more (preferably three to five) pump modules in a row. Console modules that are not pumps may also be utilized, such as the storage bin 24 which has a handle 26 for opening and closing a drawer of the bin and is attachable to the console base in a manner similar to how the console modules are attached.

Figure 1B:
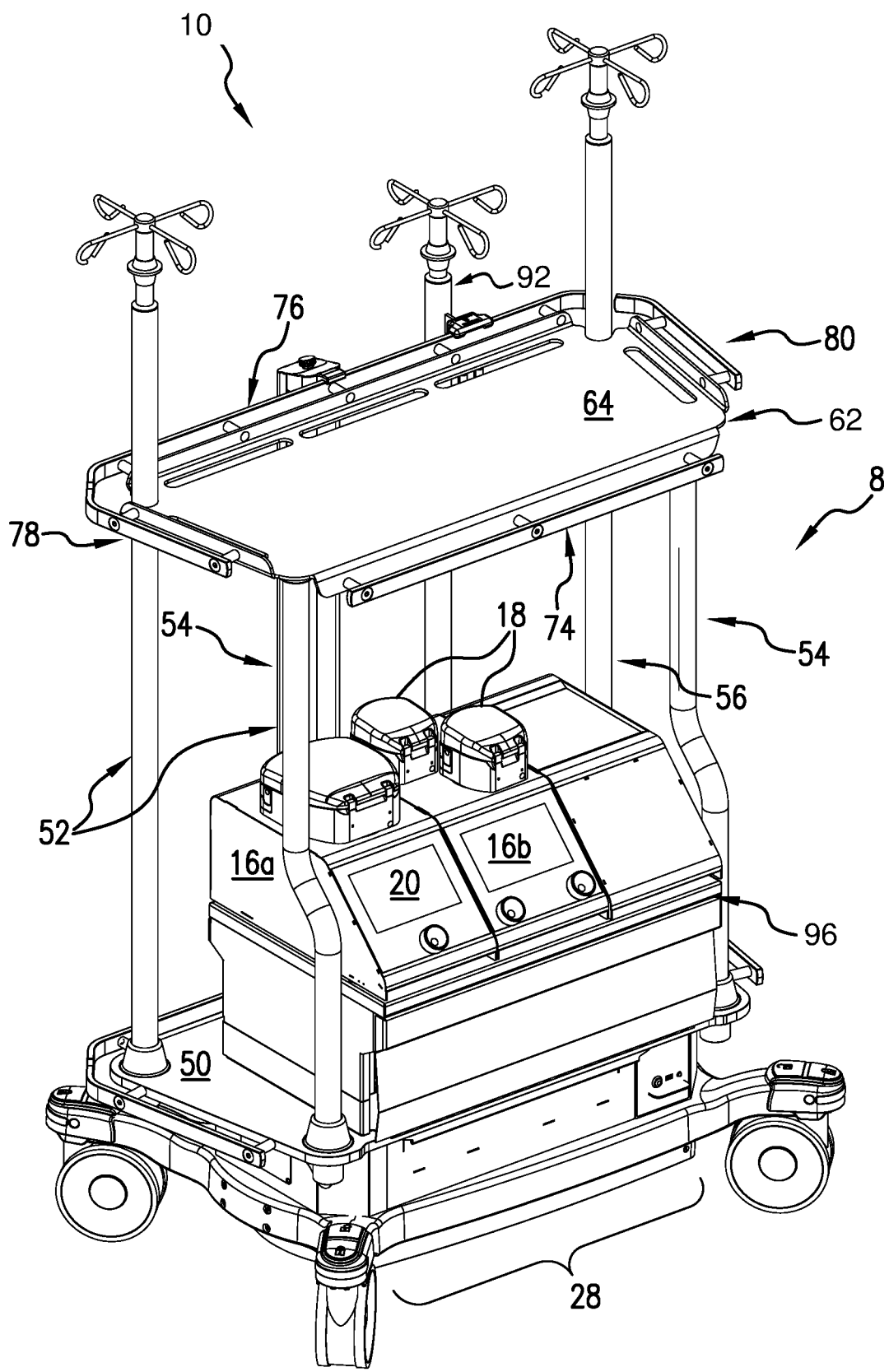
FIG. 1B is a perspective view of the medical apparatus of FIG. 1A with various detachable peripheral devices removed.
Figure 2:
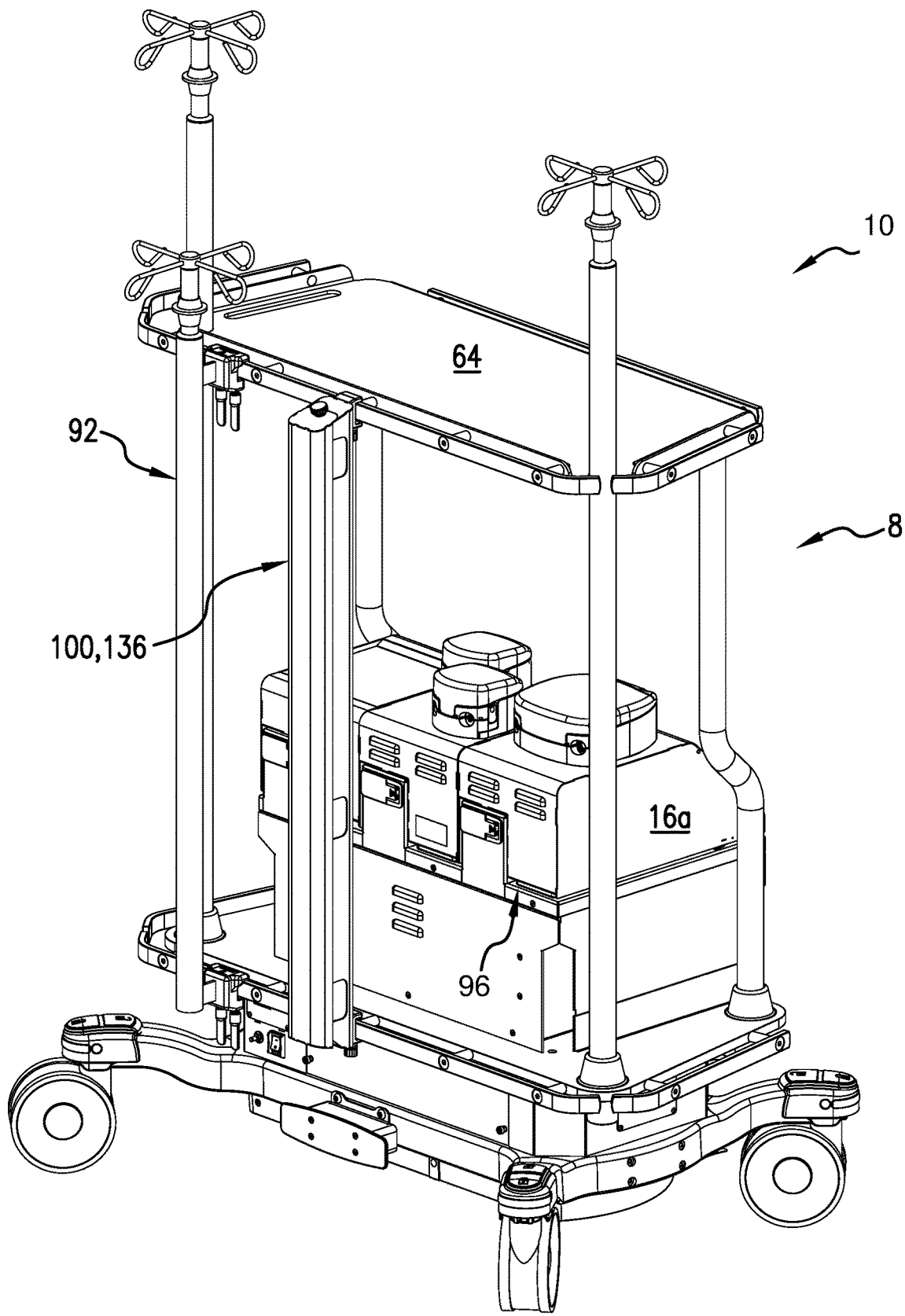
FIG. 2 is a rear perspective view of the medical apparatus of FIG. 1B, illustrating the "patient side" thereof, in accordance with an embodiment of the present disclosure.
Figure 3:
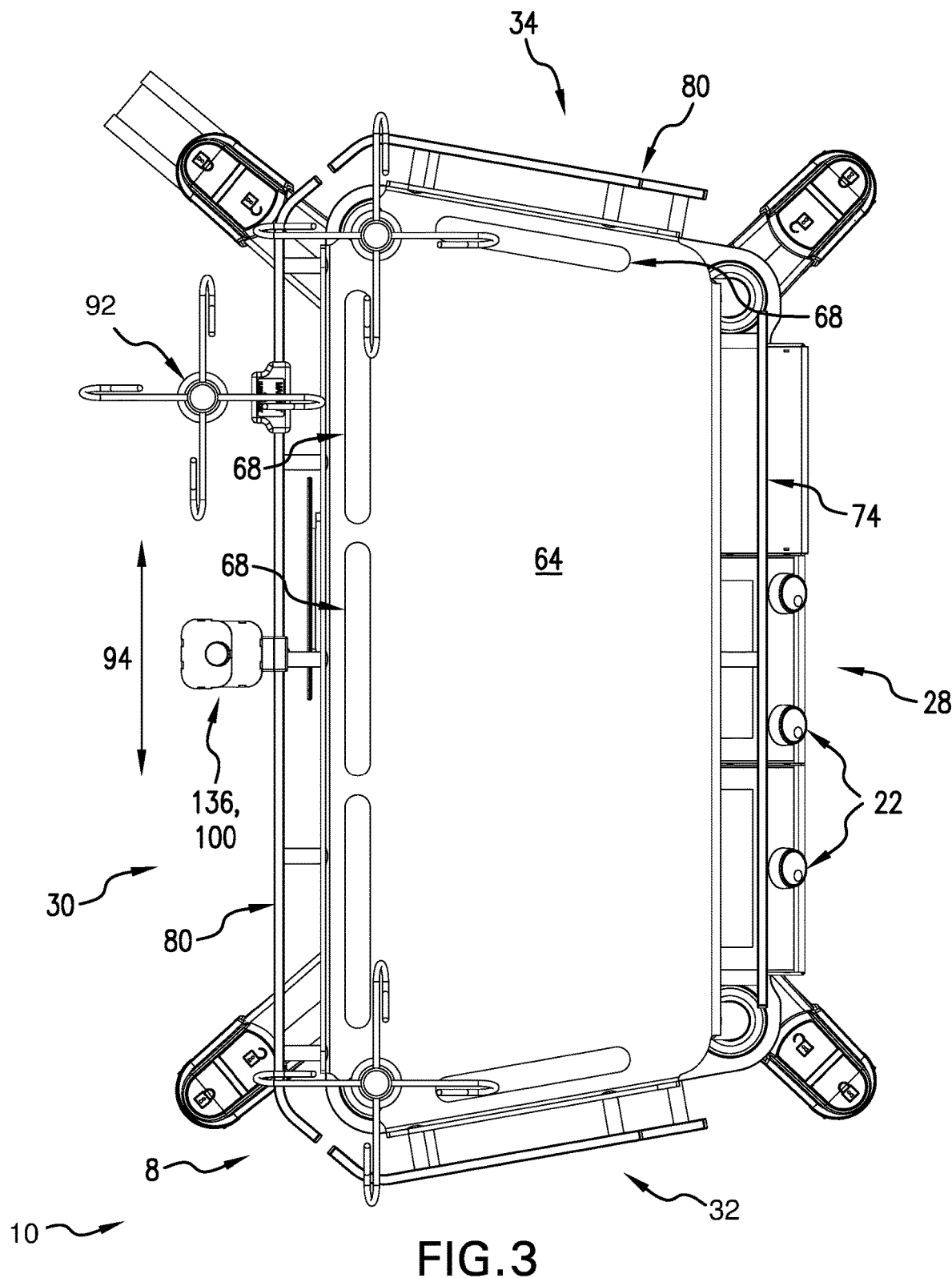
FIG. 3 is a top view of the medical apparatus of FIGS. 1B and 2, in accordance with an embodiment of the present disclosure.
Figure 4:
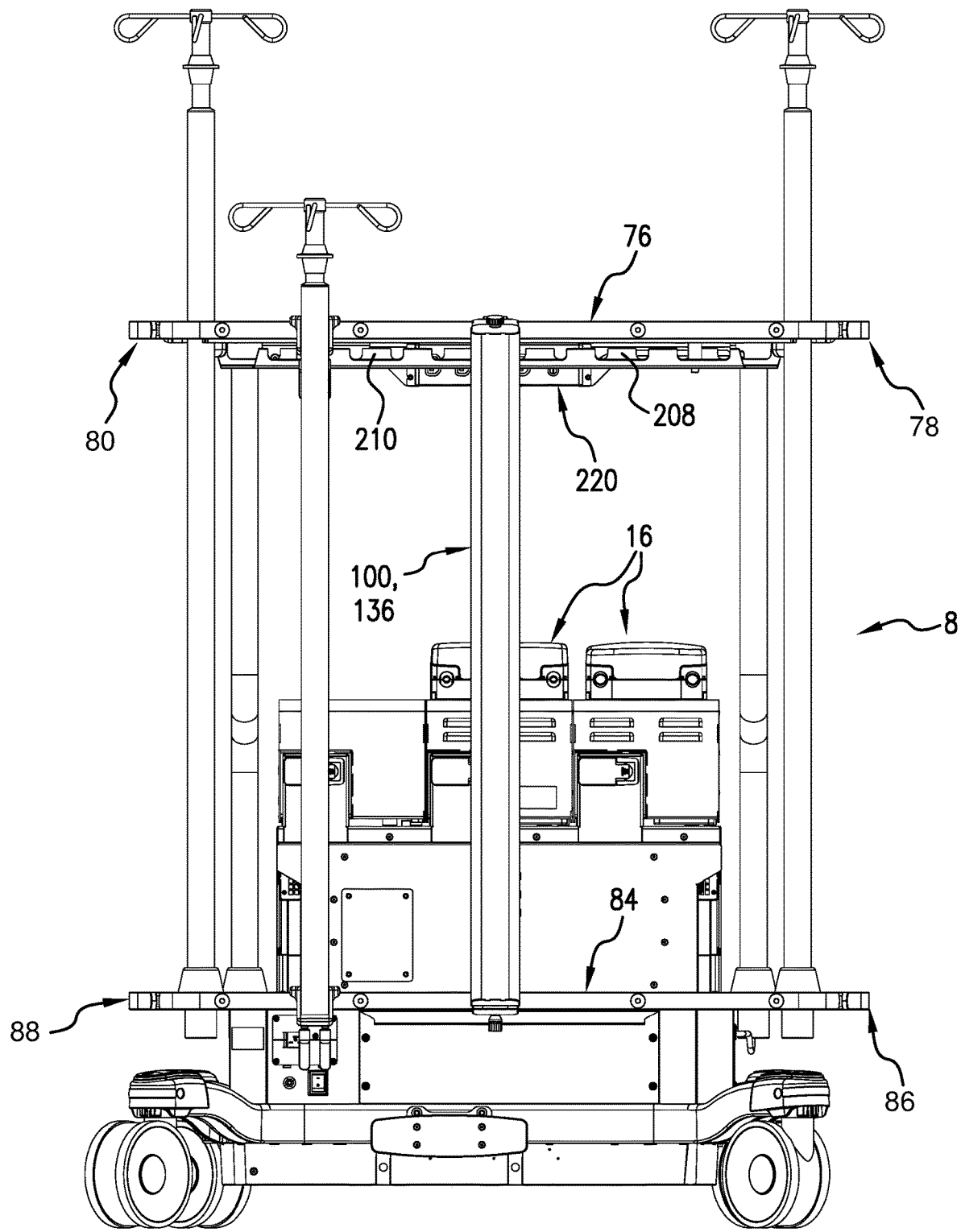
FIG. 4 is a rear elevation view of the medical apparatus of FIGS. 1B-3, presenting the "patient side", in accordance with an embodiment of the present disclosure.

The displays 20 for the console pumps are generally orientated to be visible from the "operator side" 28 of the console 8, and opposite the "patient side" 30 (see FIG. 2). The console pumps may be controlled directly by an operator or through a primary module display 6 (see FIG. 1) to the extent the display 6 includes control functionality as for example may be implemented via a touch-screen interface. The console 8 is shown in the figures to have a plurality of masts 52 that extend vertically from a frame support surface 50 to a shelf 62. The masts 52 are generally fixed with respect to the frame and support surface 50, and are useful for having directly or indirectly attached to them various peripheral attachments such as mast-mounted pumps 170.

As shown in FIG. 1A, the fixed masts 52 are arranged as two front masts 54 and two rear masts 56, of which the front masts 54 terminate with and support the underside of an elevated shelf 62 while the rear masts 56 connect with and extend vertically through the shelf 62 and further comprise an IV pole top with a plurality of IV hooks. There may also be one or more auxiliary masts 242 that extend from the rear masts 56 via one or more mast extension(s) or boom(s) 244. The versatility offered by having additional masts provides the operator with a seamless unlimited amount of arrangements in which additional peripherals such as pumps can be included in the operational setup of the medical apparatus when configured as a heart-lung machine.

In addition to the use of masts to mount certain peripheral devices, certain devices may be conveniently located on additional working surface areas such as a top-shelf 62 or a detachable shelf 240. The detachable shelf 240 is shown in FIG. 1 to be reversibly mounted to one of the upper or lower rails, and is shown by example in FIG. 1 to be attached to a base rail 88 as will be described in more detail below.

Located vertically above the console pumps 16 is a shelf 62, which is shown to have a generally flat surface top surface 64 with upwards turning lips on the rear and lateral sides, and a downward turning lip on its front side (i.e., operator side). Attached to the lips are a plurality (i.e., a first upper set) of rails surrounding the perimeter of the shelf 62. While four rails are shown, more or fewer may be used. The rails may have any type of cross-sectional shape, such as a square, circular, oval, elliptical, rectangular, etc., and preferably may have a substantially rectangular cross-sectional shape. More specifically, shelf 62 is shown with two upper side rails 78, 80, one rear rail 76, and one front rail 74. The front rail is shown to be at a lower elevation than the top surface 64 of the shelf 62, while the side and rear rails are shown to be slightly elevated or at the elevation of the shelf's top surface 64.

A second (i.e., lower) set of rails is shown attached to the frame support surface 50. Three rails are shown, of which two side rails 86, 88 and one rear rail 84 are spaced about the sides and rear edge of the frame support surface 50 respectively. Optionally, the rails may be bent at their ends to conform with the corners and overall perimeters of the frame support surface 50 and shelf 64, while in other regions the rails are substantially straight.

FIG. 2 illustrates the patient side of the console 8. Extending generally vertically between the shelf 62 and the frame support surface are a moveable mast 92 and a cable chase 100,136. The cable chase 100, 136 and moveable mast 92 may be reversibly or irreversibly secured to the console 8 through a connection with one or both of the upper set of rails and the lower set of rails. The connection may be lockable such that either or both of the moveable mast 92 and cable chase 100, 136 may be restricted (fully, partially, or selectively) from horizontal side-to-side movement (shown by arrows 94 of FIG. 4) along the length of the rails (e.g., along the patient side 30), as otherwise may be possible without a lock.

The cable chase 100, 136 is shown in FIG. 2 to have one or more chase apertures 112 such that cables/cords/tubes, etc. may enter and exit the cable chase at different elevations with respect to the console 8. For example, an aperture 112*a* may be located towards the top of the cable chase/raceway 100, 136 to provide access to cables located above or below the shelf 62. In another example an aperture 112*b* may be located towards the bottom of the cable chase to provide access to cables exiting the base 12 of the console 8. Additional apertures (112*c*, 112*d*) may exist between the top and bottom portions of the cable chase. While the apertures are shown to be located on the sides of the cable chase, they can alternatively and/or interchangeably be located at the upper and lower ends of the cable chase, or along a different sidewall portion of the cable chase.

Figure 5:
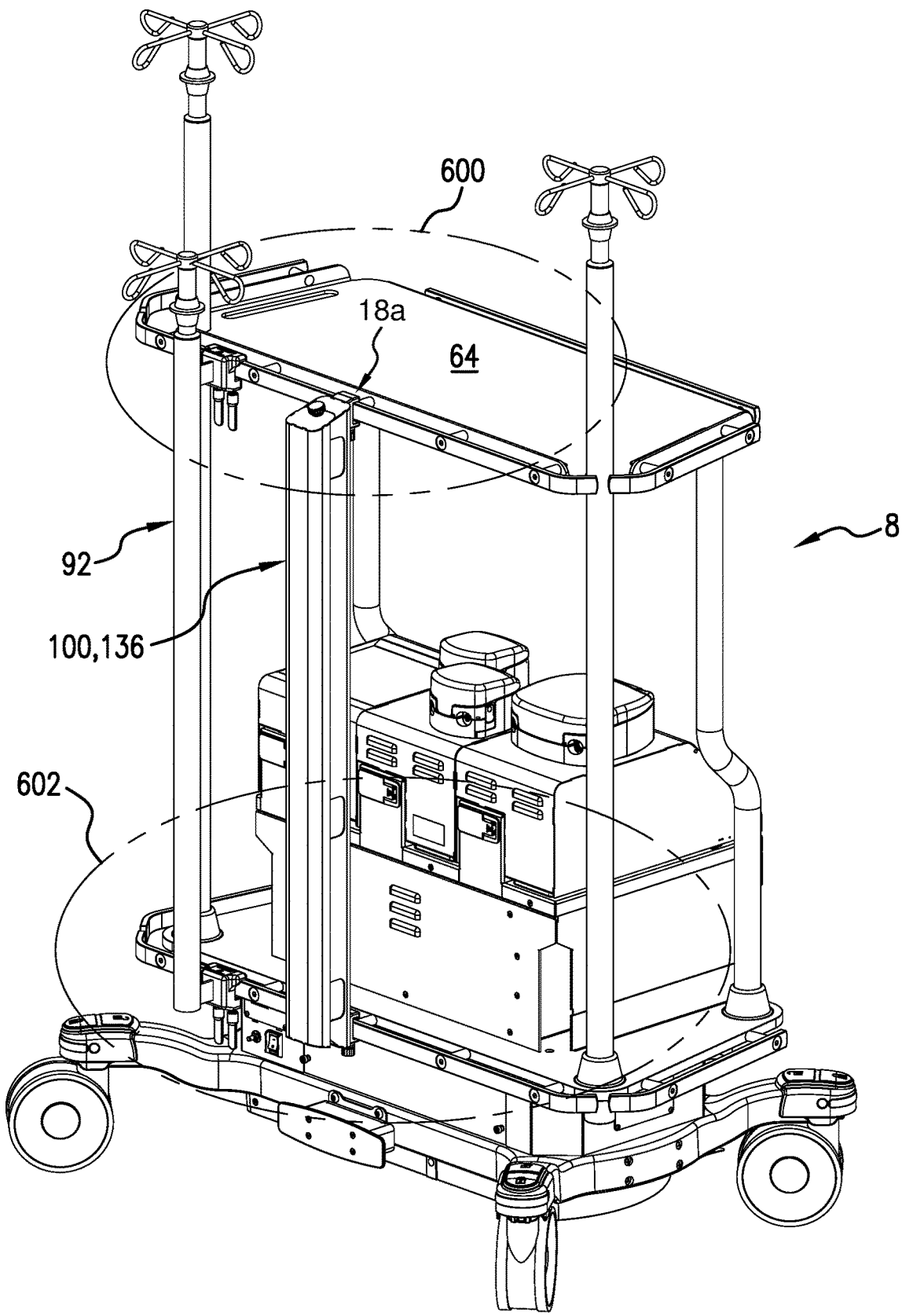
FIG. 5 is another rear perspective view of the medical apparatus of FIGS. 1B-4, similar to the view of FIG. 2.
Figure 6A:
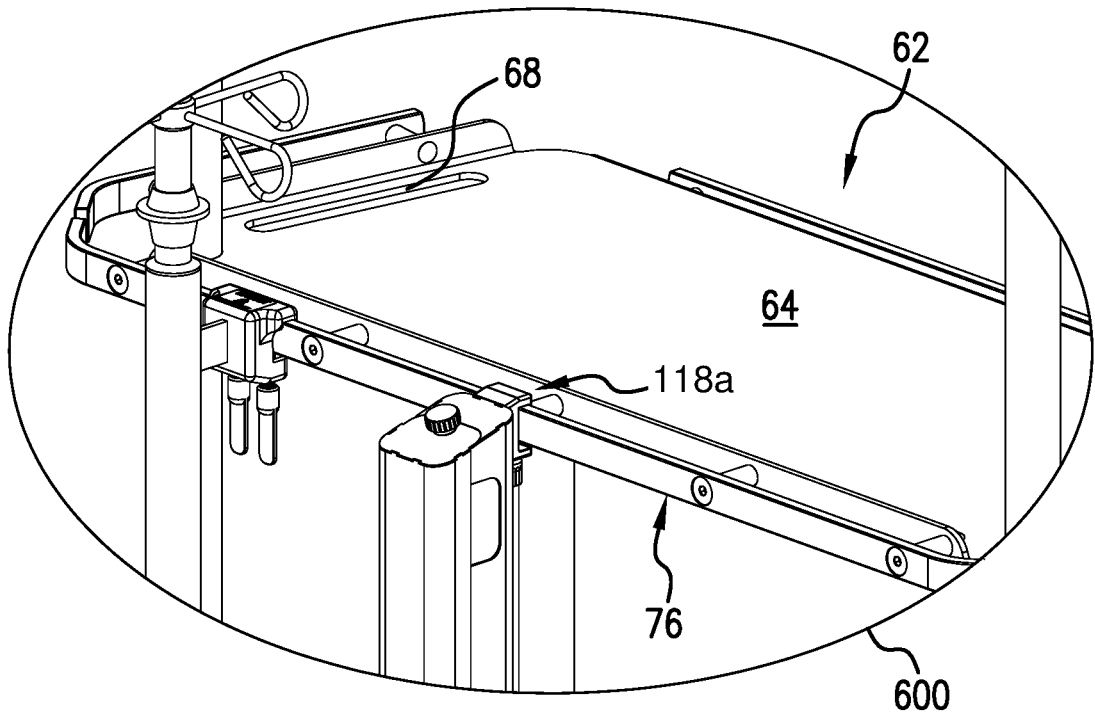
FIG. 6A is a detail view the medical apparatus of FIG. 5 taken about border 600 of FIG. 5.
Figure 6B:
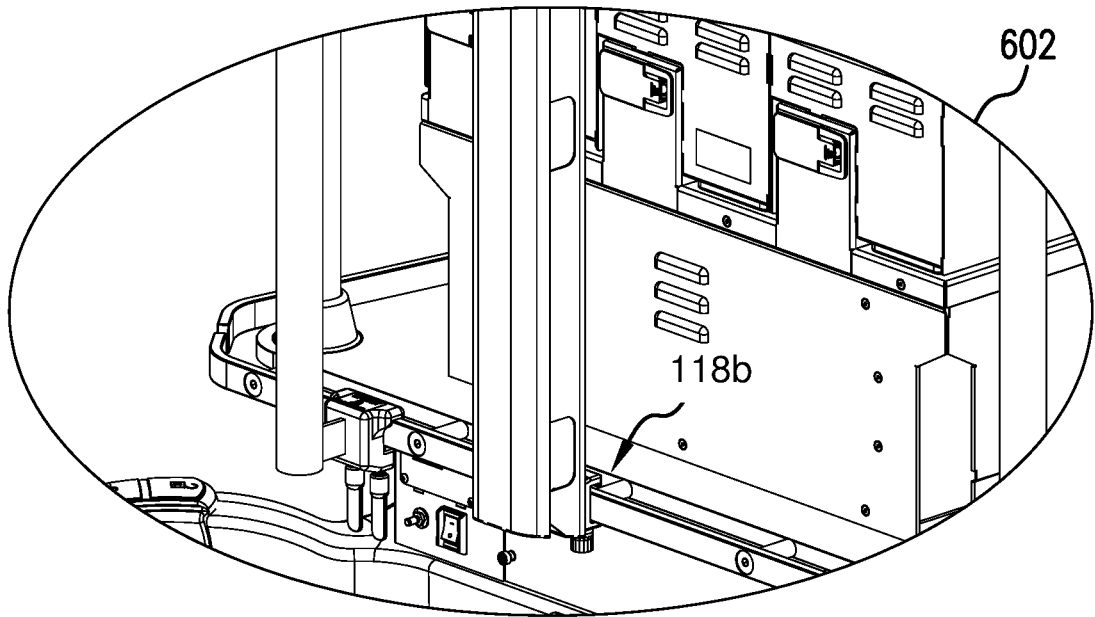
FIG. 6B is a detail view of the medical apparatus of FIG. 5 taken about border 602 of FIG. 5.

FIG. 5 illustrates another view of patient side of the console 8 and comprises an upper border 600 and a lower border 602 in which detail views 6A and 6B provide a close-up view of an example means for connecting the cable chase 100, 136 to the rear shelf rail and the rear base rail respectively. By specific example, the connecting means is shown to be a mechanical clamp such as a C-shaped clamp. Other ways of connecting the cable chase to the console are of course understood to be usable, including for C-shaped clamps that are adjustable or may be configured with a compliant material to be flexible.

Figure 7:
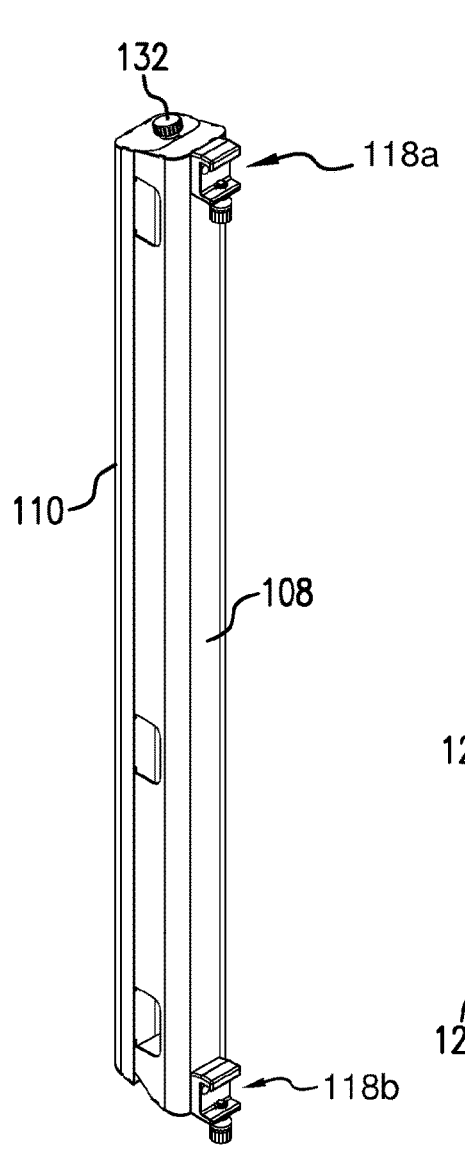
FIG. 7 is a perspective view of a cable chase/raceway according to an example embodiment of the present disclosure.
Figure 8:
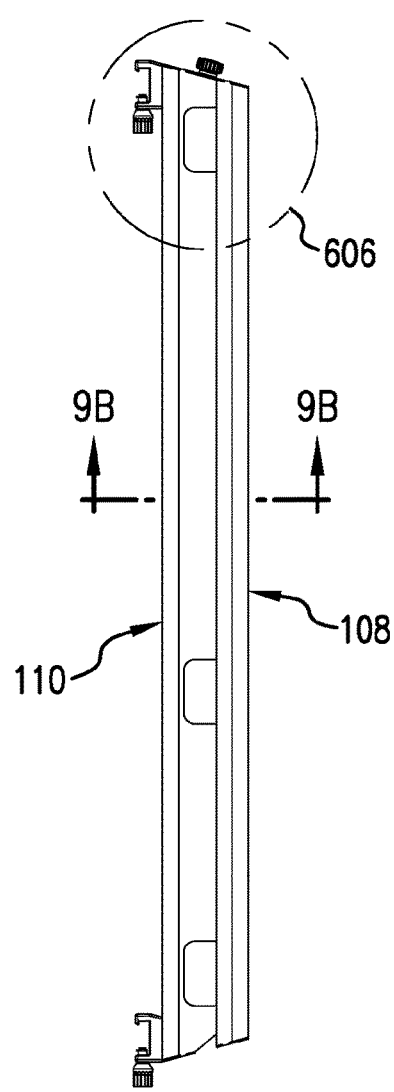
FIG. 8 is a side elevation view of the cable chase of FIG. 7.

FIG. 7 illustrates a perspective view of the cable chase 100, while FIG. 8 illustrates a side view of the embodiment of FIG. 7. In an example embodiment, the cable chase has a top end 104 and a bottom end 106 and a chase body or housing 108 extending therebetween, which provides for an internal chase raceway (or channel) 102 that provides for a partially or fully confined space in which cables, cords, tubing, and the like can extend along. The ends of the cable chase are shown to be closed, but alternatively may be open. Also shown in FIG. 7 is an optional chase cover 110. In certain embodiments, the chase cover 110 fits over a housing portion 108, and may further enclose the chase raceway 102 and confine cord/cable/conduit-like structures that are routed through the cable chase (see FIG. 9B for an area cross-sectional view of the raceway taken about sectional lines 9B-9B of FIG. 8). The cover may also be used to enclose an open side of apertures 112 (*a, b, c*). In various embodiments the cover 110 may be attached along a vertical/longitudinal edge of the chase body by a hinge to act as a door, while in other embodiments the cover may be attachable to the chase body 108 by one or more reversible connection mechanisms, including but not limited to the use of clamps, hook and loop (VELCRO) surfaces, latches, screws, knobs, pins, etc.

Figure 10:
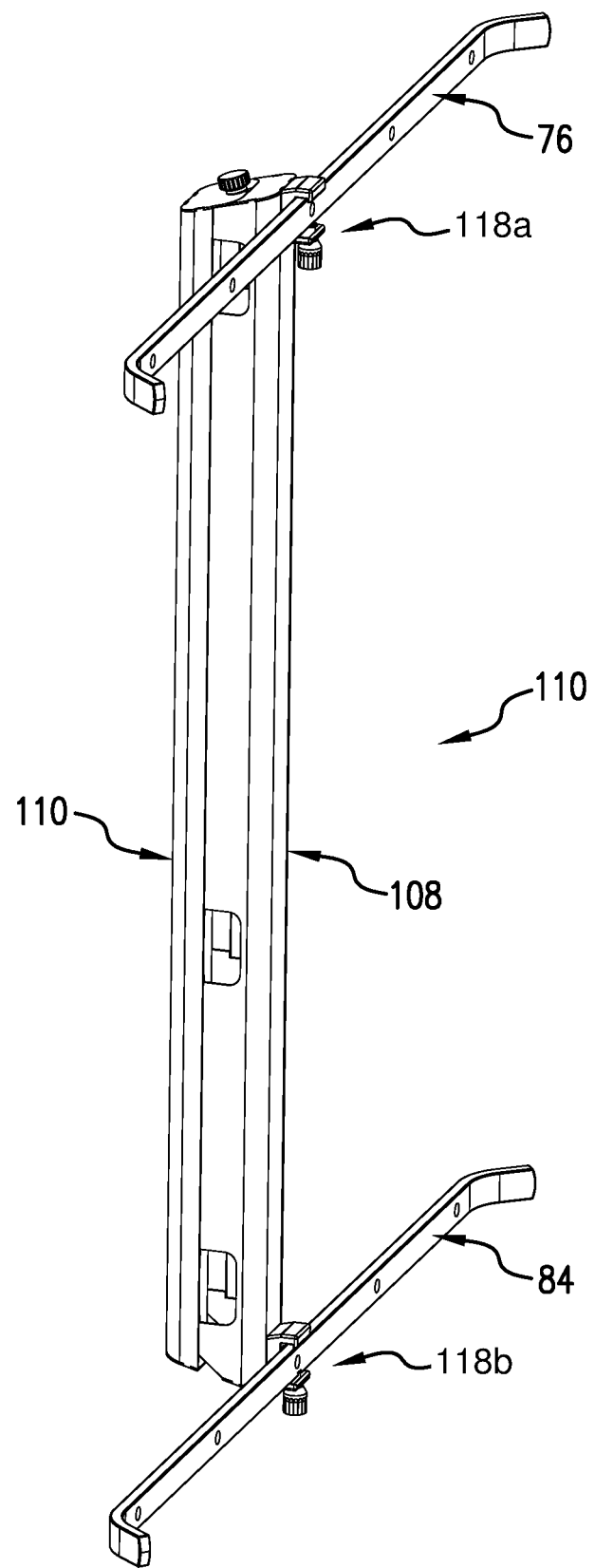
FIG. 10 is a perspective view of an example embodiment of a cable chase attached to an upper and lower rail of a medical apparatus, with other portions of the medical apparatus not displayed.

FIGS. 7 and 8 further illustrate by example an attachment means for attaching the cable chase 100 to the console 8 through the use of one or more of the rails mounted to the console 8. An upper clamp 118*a* is shown at the top end 104 of the cable chase, and a lower clamp 118*b* is shown at the bottom end 106. The clamps may be of the same or different types, and are shown by example to be "C" shaped clamps with a knob for reversibly tightening the clamp about the rail by compressing the rail between a threaded knob 120 and an opposing "arm" 122 of the C-shaped clamp 118. FIG. 10 illustrates the clamps in use with the upper 76 and lower 84 rear rails. One of ordinary skill in the art would recognize that the side rails may be used alternatively or in addition to the rear rails, in the event the user prefers to establish one or more raceways along different portions of the console 8.

Figure 9A:
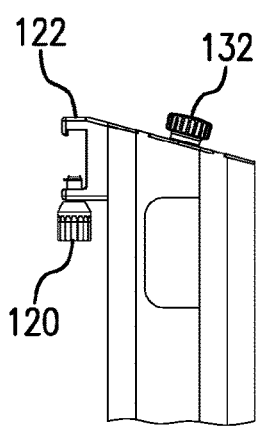
FIG. 9A is a detail view of the top portion of the cable chase of FIG. 7 taken about border 606 of FIG. 8.

FIG. 9A relates to a detail view of FIG. 8 taken about border 606, and further illustrates the top portion of the cable chase according to an example embodiment. A knob 132 is shown which helps secure the cover 110 to the base 108 so that the cable cover 110 cannot get knocked off of the base 12 if a surgeon or assistant accidentally knocked into the cable chase 100 during a surgical procedure. Other means for securing the housing or chase body 108 and cover 110 components together are also contemplated, with preference for a reversible mechanical securement means.

Figure 12:
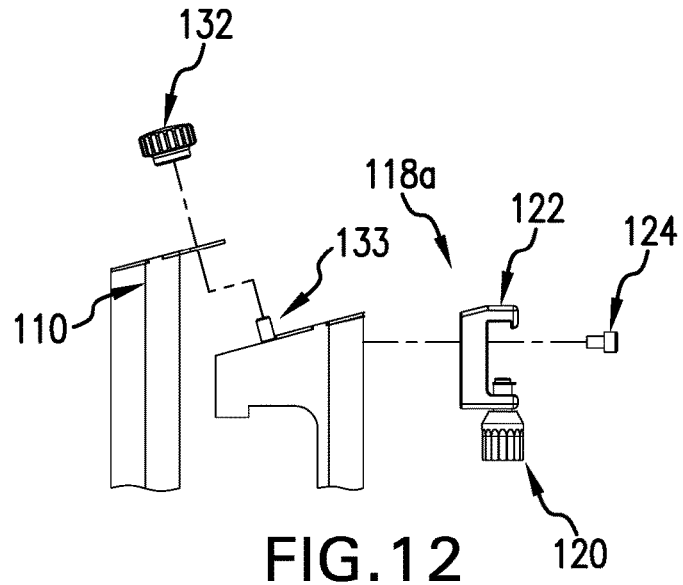
FIG. 12 is an exploded perspective view of the upper portion of the cable chase of FIG. 11 illustrating the attachment of the cover to the chase body, according to an example embodiment.
Figure 11:
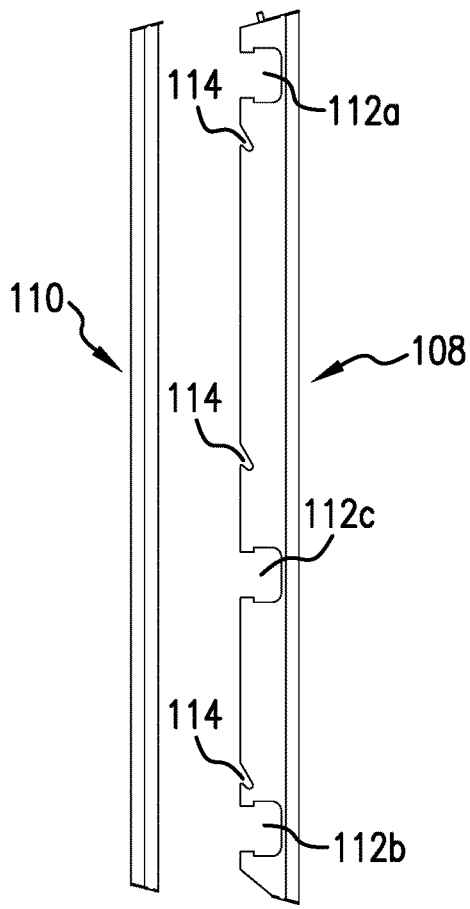
FIG. 11 is an exploded side elevation view of the cable chase of FIG. 10.
Figure 13:
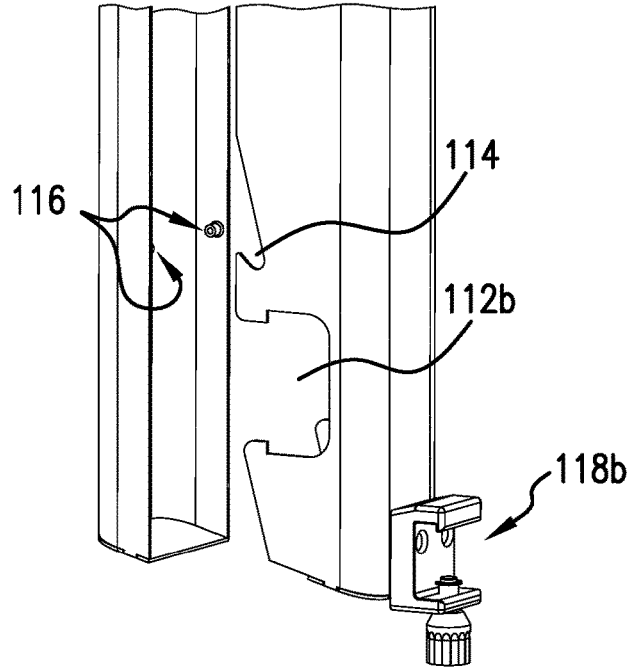
FIG. 13 is an exploded perspective view of the lower portion of the cable chase of FIGS. 10 and 11, with the lower clamp further included, according to an example embodiment.

While FIGS. 7 through 10 illustrate the chase cover 110 attached to the chase body 108, FIGS. 11 through 15 illustrate the various exploded views with the chase body 108 detached from the chase cover 110. Also, while various means of attaching the cover to the chase body 108 are contemplated, a particularly useful embodiment involves the utilization of angled and upwards opening slots on one of the cover 110 or body 108, and a set of guide pins 116 on the other of the cover or body. The pins 116 can slide into the slots 114 once aligned, and retain the cover 110 with respect to the body 108 under the force of gravity. Additionally, a post 133 may be located at the top end of the chase body 108 to engage a threaded knob 132 to assist in retaining the cover 110 with respect to the chase body 108. As best shown in FIG. 12, the c-shaped clamp(s) may be connected to the chase body 108 by a variety of means, such as the use of screws or adhesive. Alternatively, the c-shaped clamp structure can be integrally formed with the chase body 108.

Figure 14A:
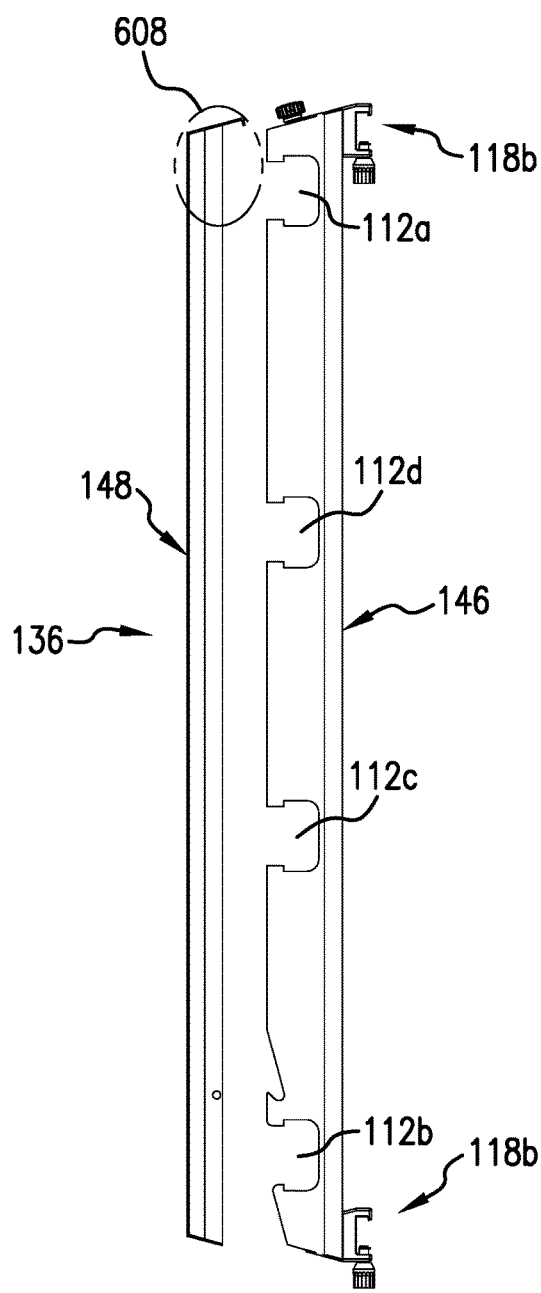
FIG. 14A is an exploded elevation sectional view of a cable chase taken about sectional lines 14A of FIG. 15, according to an example embodiment of the present disclosure.
Figure 14B:
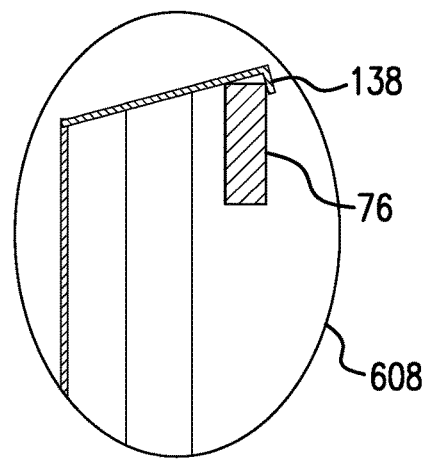
FIG. 14B is a detail view taken about border 608 of FIG. 14A.
Figure 15:
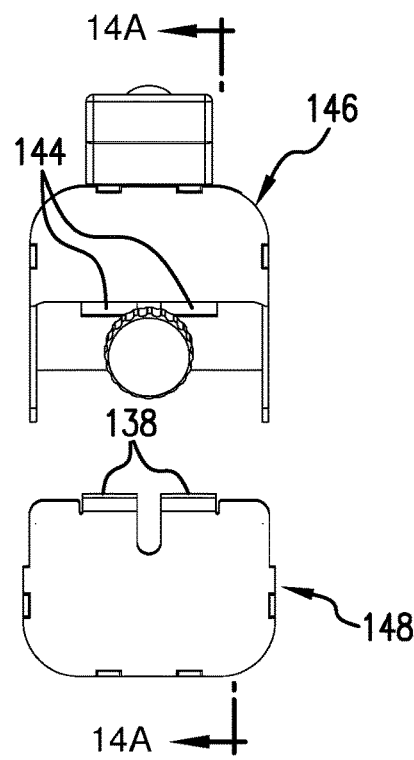
FIG. 15 is a top view of the cable chase of FIG. 14A.

FIGS. 14-15 illustrate an embodiment of a cable chase 136 that has certain enhancements as compared to the embodiments described heretofore. FIG. 14B is a detailed view taken about border 608 of FIG. 14A and shows a latch or hook 138 located on the top end of the chase cover 148. FIG. 14B differs from FIG. 14A in that a cross-section of a rail 76 is shown, for which the hook 138 has a gape and throat sufficient to be hung on the rail 76. The hook 138 may be configured as one or multiple hooks, and can further be used to assist in the connection of the cover 148 to the chase body 146 via the insertion of the ends of the hook(s) at least partially into one or more slots 144 located in the chase body 146. Similar to the embodiment of FIGS. 5-13, a mechanical securement mechanism such as a threaded screw knob can be used to further secure the cover 148 to the chase body 146. Also, while the embodiments of FIGS. 5-13 illustrated three apertures 112, a fourth aperture 112d may also be employed in any of the cable chase embodiments described herein, as more clearly shown in FIG. 14A.

Figure 16:
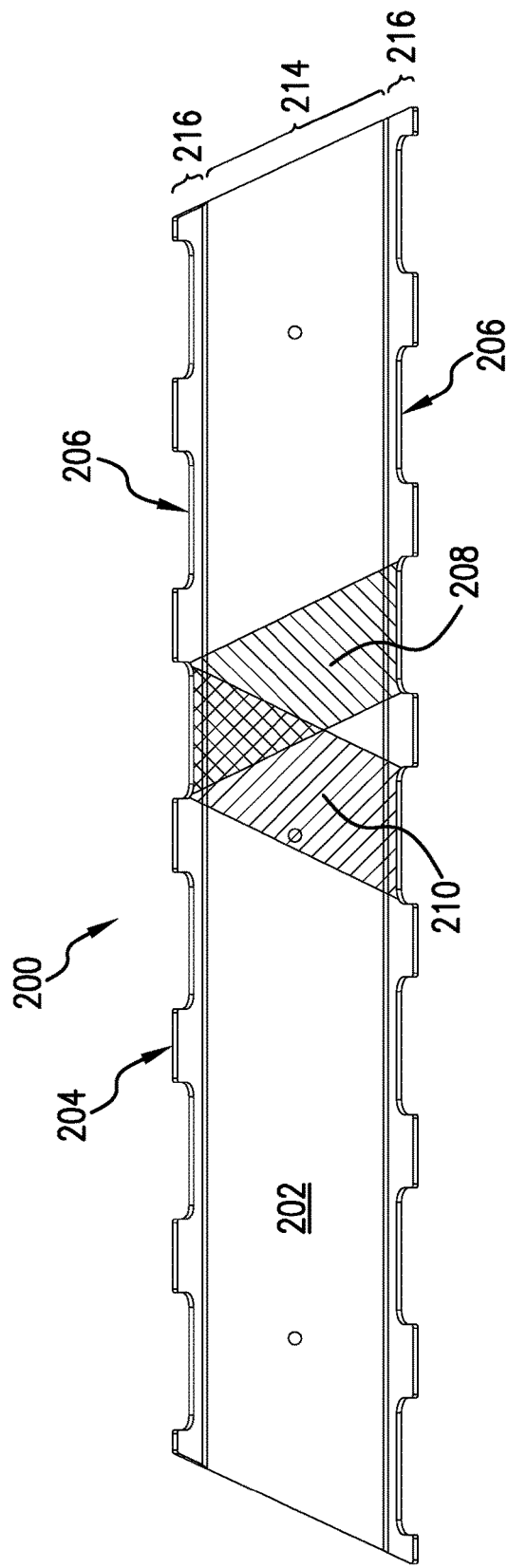
FIG. 16 is a top view of a cable/conduit holder according to an example embodiment of the present disclosure.
Figure 17:
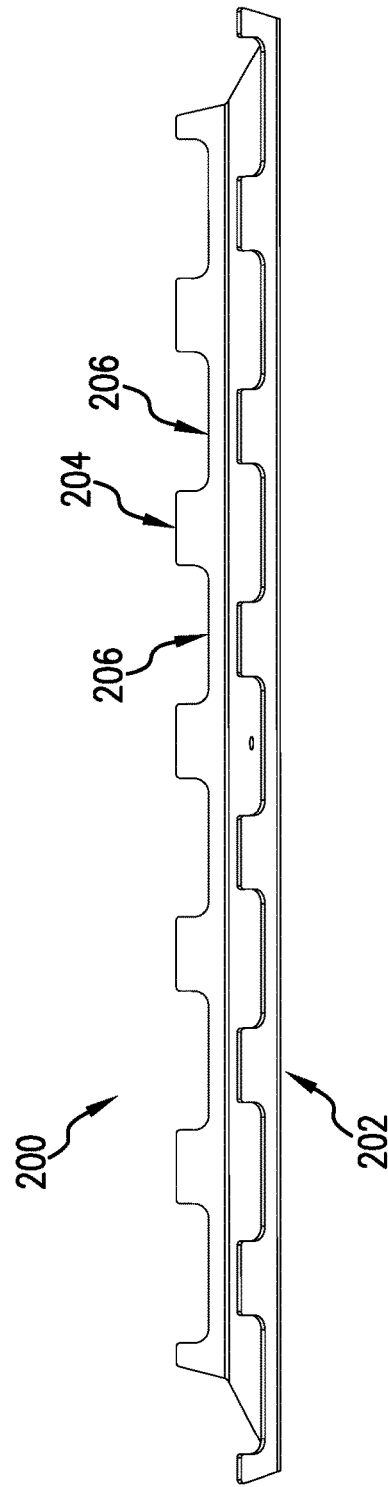
FIG. 17 is a front perspective view of the cable holder of FIG. 16.
Figure 18A:
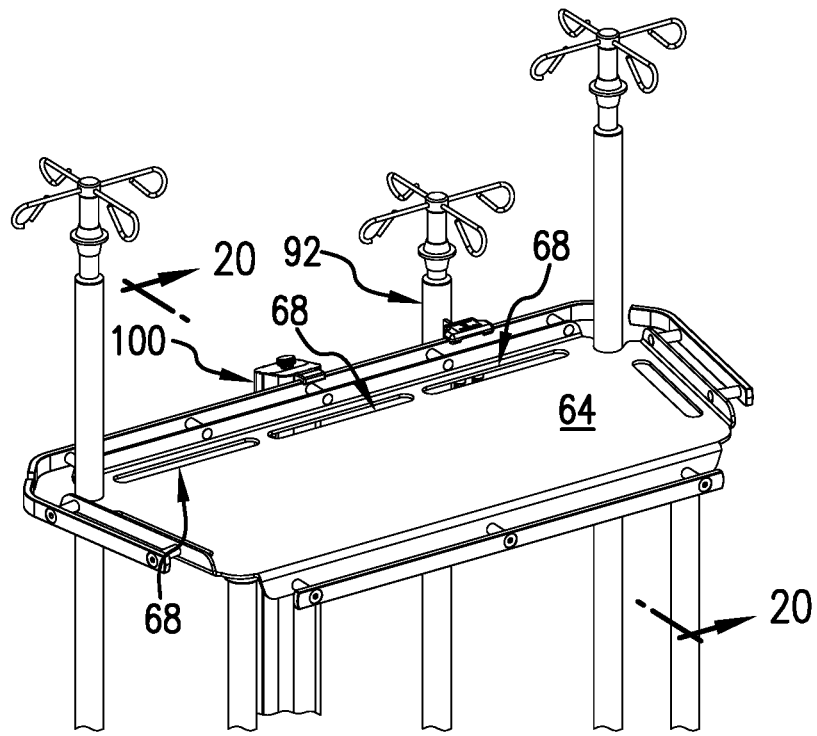
FIG. 18A is a perspective detail view of the top portion of the medical apparatus of FIG. 1B.
Figure 18B:
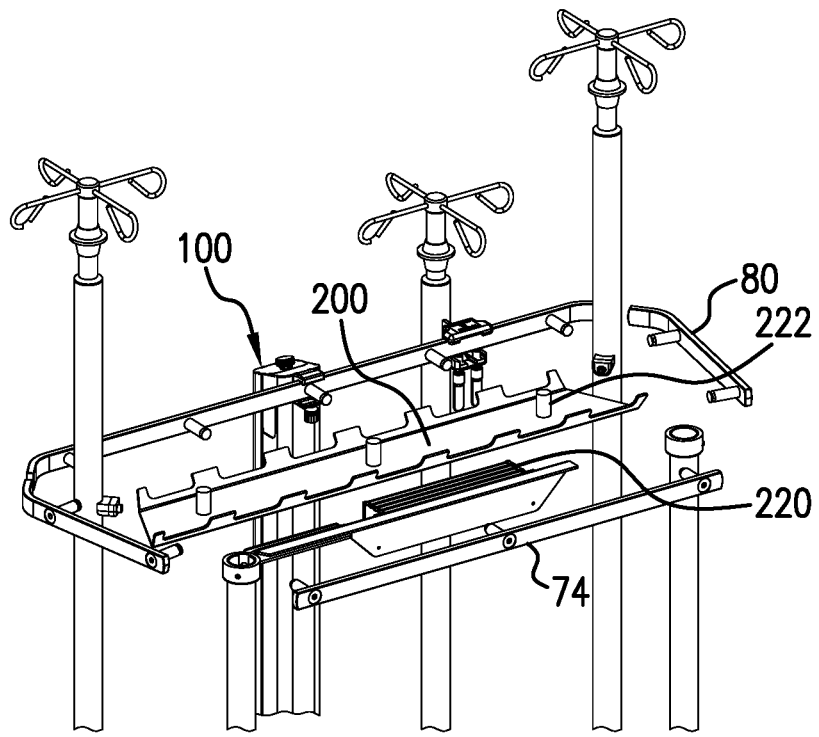
FIG. 18B is similar to the view of FIG. 18A, with a shelf removed for providing clarity to those features that would otherwise be obscured by the shelf.

FIGS. 16-20 illustrate a further feature of the present disclosure that may be employed with or without the cable chase embodiments 100, 136 described herein. For example, FIG. 16 illustrates a top view of a cable holder 200, while FIG. 17 shows the cable holder 200 in a front elevation perspective view with other structures of the console 8 not shown. The holder 200 is shown to be formed as a shallow U-shaped channel 202, with a base portion 214 interposed between two legs portions 216. The base portion may have a width substantially wider than the height of the leg portions. The holder 200 may be elongate and comprise a plurality of cutouts 206 formed in the leg sections 216 to establish a plurality of fingers 204. From one longitudinal edge of the holder 200 to the other longitudinal edge, the fingers 204 can form one or more passages such as first passage 210 and second passage 212, as shown in FIG. 16. The cable holder 200 may be secured to the shelf 62 in a suspended manner as shown in FIGS. 18A, 18B, 19 and 20. One or more standoffs 222 such as shoulder-bolts may be used to accomplish this. In alternative embodiments, the shelf may be attached to one or more of the masts and extend (such as in a cantilevered manner) underneath the shelf 62. An optional feature in all of the shelf embodiments disclosed herein are the use of shelf apertures or shelf channels 68 which provide convenience in routing cables through the shelf instead or if needed in addition to be routed around the perimeter of the shelf.

Figure 19:
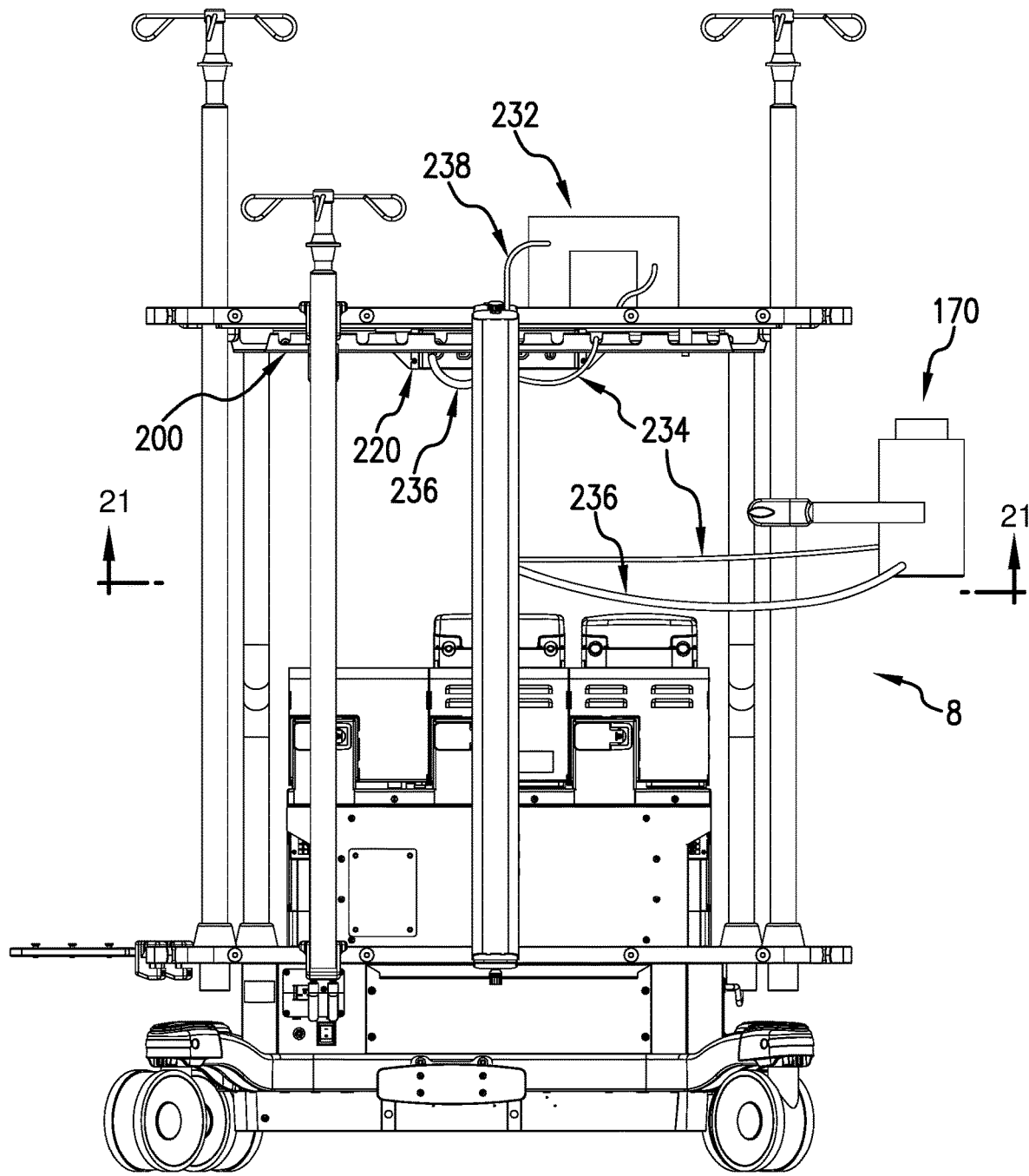
FIG. 19 is a rear elevation view of a medical apparatus according to an example embodiment of the present disclosure, showing a mast pump connected to a mast and related example cable routing.
Figure 20:
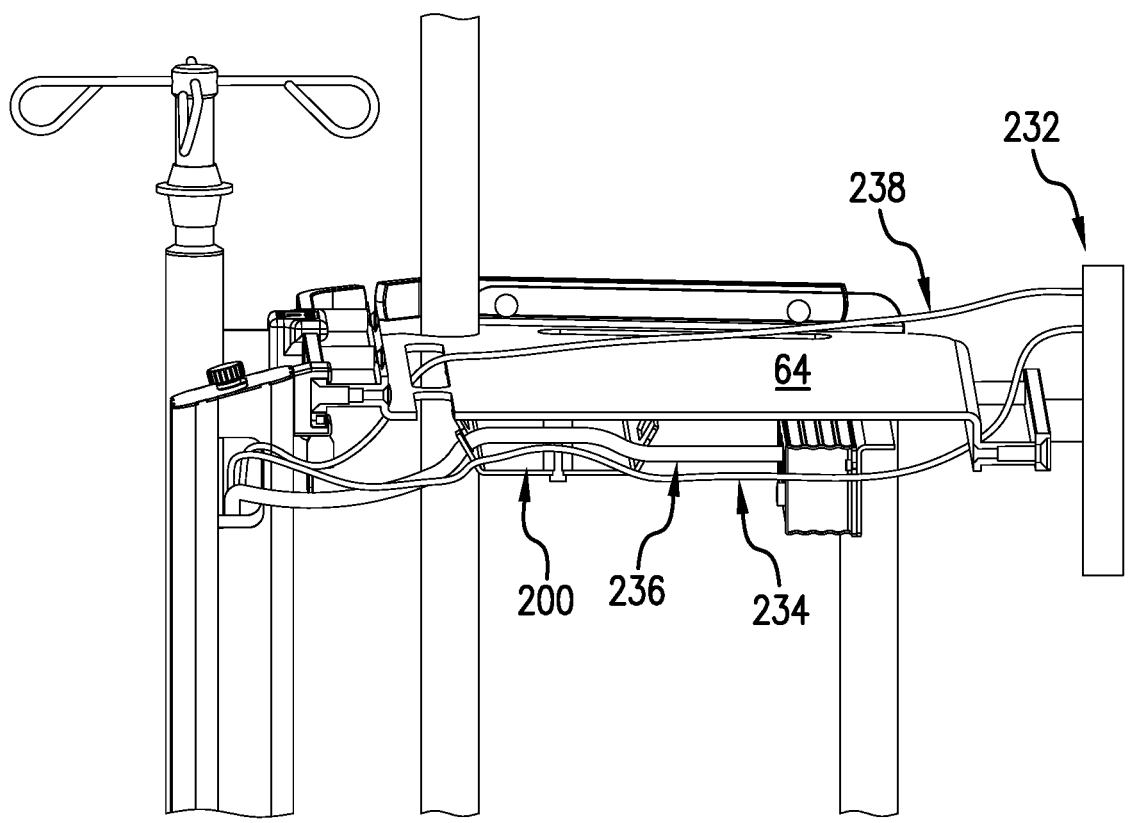
FIG. 20 is a cross-sectional view taken about sectional line 20-20 of FIG. 18A.
Figure 21:
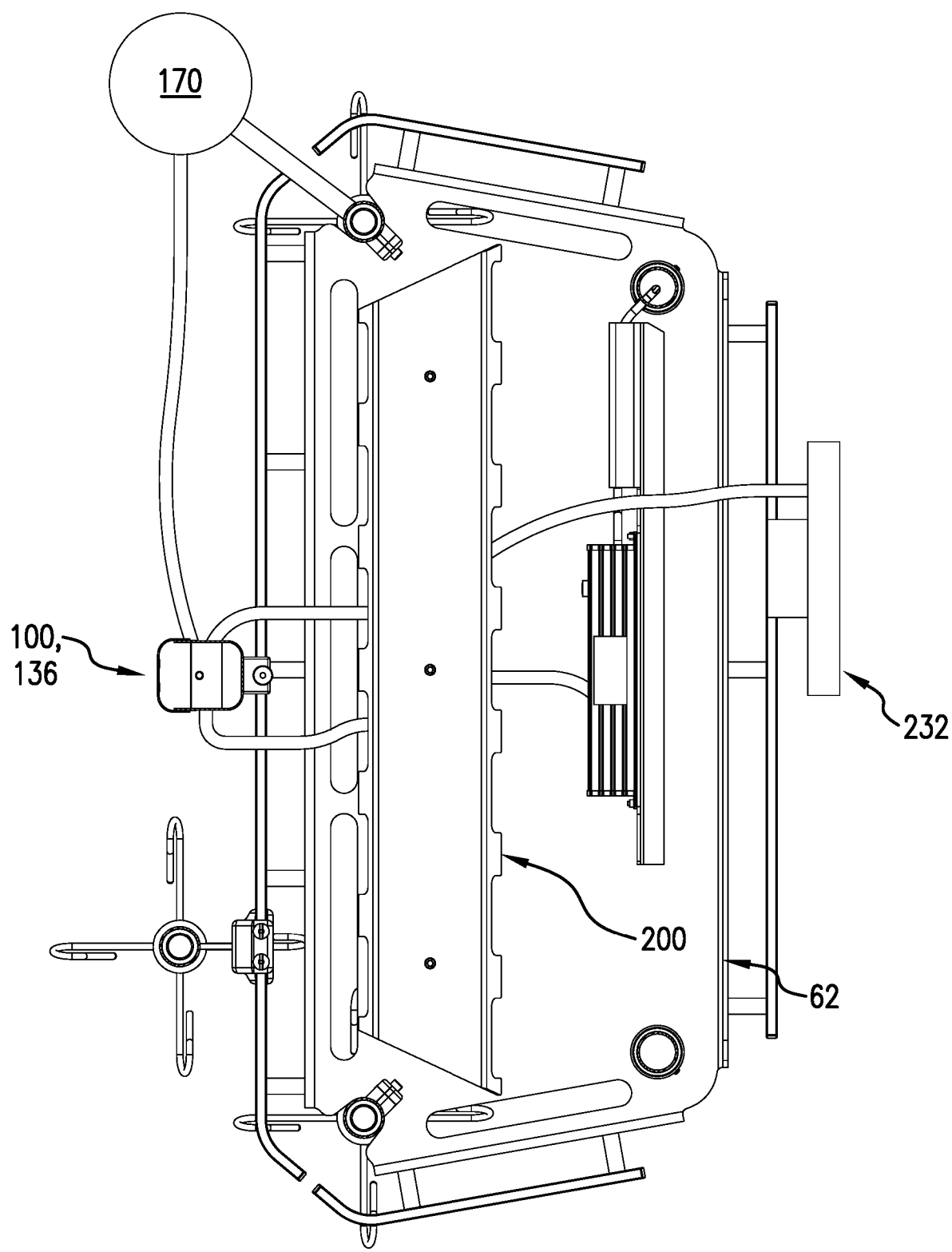
FIG. 21 is bottom view of that portion of the medical apparatus of FIGS. 18A and 18B and 19, taken about line 21-21 of FIG. 19, and with the bottom portion of the medical apparatus removed to provide visibility to the underside region of the shelf.

FIGS. 19-21 represent a non-limiting example of the cable holder 200 in use with the cable chase 100, 136. The peripherals used in the disclosed example may include an auxiliary display 232 used to monitor and control a mast mounted pump 170. FIG. 19 shows an auxiliary display 232 mounted to the shelf front rail 74 and the mast mounted pump 170 attached to one of the vertical masts (e.g., fixed mast 52). Other variations of auxiliary display 232 mounting may of course be possible, such as the embodiment shown in FIG. 1A. Many alternative arrangements are contemplated that may be specific to the design, construction, function and use of the peripherals.

As shown in FIG. 19, a first cable 234 connects the display to the mast pump, while a second cable 236 connects the pump 170 to a power strip 220. For example, a further cable 238 may be necessary to connect the display 232 to a main module connection station (not shown), which may for instance be located in the base of the console 8 and accessible towards the operator side 28 of the console 8 by opening a front panel access door 38. As shown in the figures, the cables 234, 236 are routed underneath the shelf 62 and through one of the passages 208, 210 of the cable holder 200, and then into the raceway/channel 102 established by the cable chase 100, 136. In light of the versatile construction of the embodiments taught herein, improvements to the use, set up time, and operation of the medical apparatus system 10 can be achieved, especially but not limited to an improved use in the field of cardiopulmonary bypass.

While systems and methods have been described with reference to certain embodiments within this disclosure, one of ordinary skill in the art will recognize, that additions, deletions, substitutions and improvements can be made while remaining within the scope and spirit of the invention. Additionally, while the use of embodiments of the present disclosure may be beneficial to the application of perfusion for living mammals and humans, the same can be used for non-human subjects, including medical simulators, test or training mannequins, and the like.

The invention claimed is:

1. A cardiopulmonary bypass system comprising:
   a cardiopulmonary bypass machine comprising a console, the console comprising a base and a frame connected to the base;
   a plurality of peripheral modules operatively connectable to the cardiopulmonary bypass machine; and
   a cable chase comprising a first end and a second end, and a cable chase housing that extends at least partially between the first end and second end and at least partially encloses a channel for receiving one or more cables or conduits connected to at least one of the plurality of peripheral modules,
   wherein the base comprises a console pump support surface for supporting a plurality of console pumps, and wherein the frame comprises a shelf that is elevated with respect to the console pump support surface, and wherein the channel is configured to attach to one or both of the base and the frame, and
   wherein a cable holder is suspended from an underside of the shelf and comprises a plurality of fingers extending upwards from a channel body to provide for one or more passages for cables or conduits to be secured underneath the shelf.

2. The cardiopulmonary bypass system of claim 1, wherein the plurality of peripheral modules are selected from one or more of the following: console pumps, mast mounted pumps, occlusion clamps, display monitors, and pump control monitors.

3. The cardiopulmonary bypass system of claim 2, wherein one or more of the plurality of peripheral modules are console or mast mounted pumps, and wherein the console or mast mounted pumps are either roller pumps or centrifugal pumps.

4. The cardiopulmonary bypass system of claim 1, wherein the frame comprises one or more masts connected to and extending vertically with respect to the base.

5. The cardiopulmonary bypass system of claim 1, wherein the cable chase housing comprises two or more apertures spaced apart from each other for the one or more cables or conduits to enter and exit the channel at different locations along a length of the cable chase housing.

6. The cardiopulmonary bypass system of claim 5, wherein the distance between a first of the two or more apertures and a second of the two or more apertures is greater than 4 inches.

7. The cardiopulmonary bypass system of claim 1, wherein the cable chase housing has a length that is greater than 5.0 inches.

8. The cardiopulmonary bypass system of claim 1, the cable chase further comprising a cover, wherein the cover is configured to at least partially and reversibly enclose a lengthwise portion of the channel.

9. The cardiopulmonary bypass system of claim 8, wherein the cover is elongate and extends from the first end towards the second end of the cable chase.

10. The cardiopulmonary bypass system of claim 9, wherein the cover extends the entire length of the cable chase.

11. The cardiopulmonary bypass system of claim 8, wherein the cover removably attaches to the cable chase housing.

12. The cardiopulmonary bypass system of claim 8, wherein the cover is attached to the cable chase housing and opens and closes with respect to the channel of the cable chase housing to selectively enable and restrict access to the channel.

13. The cardiopulmonary bypass system of claim 8, wherein the cover comprises a hook for reversibly attaching to an elongate rail of the cardiopulmonary bypass machine when the cable channel is affixed to the elongate rail.

14. The cardiopulmonary bypass system of claim 8, further comprising a slot located in at least one of the cover and the cable chase housing, and a protrusion on the other of the cover and the cable chase housing for aligning and mating with the slot when the cover and cable chase housing are arranged with respect to each other to cover the channel of the cable chase housing.

15. The cardiopulmonary bypass system of claim 14, wherein the slot is open at one end and is angled downwards towards a closed end of the slot such that the slot receives and retains the protrusion.

16. The cardiopulmonary bypass system of claim 14, wherein the protrusion is a pin.

17. The cardiopulmonary bypass system of claim 14, wherein at least one of the cable chase housing and the cover of the cable chase comprise a hook, and the other of the cable chase housing or the cover comprise an aperture for receiving the hook when the cover is attached to the cable chase housing.

18. The cardiopulmonary bypass system of claim 1, wherein the base comprises a console pump support surface for supporting a plurality of console pumps, and wherein the frame comprises a shelf that is elevated with respect to the console pump support surface, and wherein one or both of the base and the frame is or are configured to attachably receive the cable chase.

19. The cardiopulmonary bypass system of claim 1, wherein the cable chase is mounted to the cardiopulmonary bypass machine such that the channel extends vertically between a first elevation and a second elevation higher than the first elevation.

20. The cardiopulmonary bypass system of claim 1, wherein when mounted to the cardiopulmonary bypass machine, the channel of the cable chase extends vertically.

21. The cardiopulmonary bypass system of claim 1, wherein the cable chase is configured to be attached to the cardiopulmonary bypass machine at a plurality of locations that are horizontally disposed from each other.

22. The cardiopulmonary bypass system of claim 1, wherein the console comprises one or more horizontally mounted elongate structures, and the cable chase is configured to mount to at least one of the one or more horizontally mounted elongate structures.

23. The cardiopulmonary bypass system of claim 22, wherein the cable chase is configured to simultaneously mount to at least two horizontally mounted elongate structures that are parallel yet spaced apart from each other.

24. The cardiopulmonary bypass system of claim 22, wherein the cable chase is configured to mount to two horizontally mounted elongate structures simultaneously.

25. The cardiopulmonary bypass system of claim 22, wherein at least one of the one or more horizontally mounted elongate structures is a rail.

26. The cardiopulmonary bypass system of claim 25, wherein the second elongate structure is a rail, and wherein the first elongate structure and the second elongate structure have consistent cross-sectional profile along more than half of their lengths.

27. The cardiopulmonary bypass system of claim 22, wherein the console comprises two or more horizontally mounted elongate structures, and wherein the cable chase is configured to simultaneously mount to both of the horizontally mounted elongate structures.

28. The cardiopulmonary bypass system of claim 1, further comprising a second connector configured to permit the cable chase to be reversibly attached to the cardiopulmonary bypass machine at a location different than the first connector.

29. The cardiopulmonary bypass system of claim 28, wherein one or both of the first and second connectors are clamps.

30. The cardiopulmonary bypass system of claim 1, further comprising a first connector, wherein the first connector is configured to reversibly connect one of the cardiopulmonary bypass machine and the cable chase to the other of the cardiopulmonary bypass machine and the cable chase.

31. The cardiopulmonary bypass system of claim 1, further comprising a first connector, the first connector is configured to permit the cable chase to be reversibly attached to the cardiopulmonary bypass machine.

* * * * *